United States Patent [19]

Keldmann et al.

[11] Patent Number: 5,797,392
[45] Date of Patent: Aug. 25, 1998

[54] INHALER

[75] Inventors: Erik Keldmann, Odense; John Reipur, Klampenborg, both of Denmark

[73] Assignee: Direct-Haler A/S, Odense, Denmark

[21] Appl. No.: 785,960

[22] Filed: Jan. 22, 1997

Related U.S. Application Data

[63] Continuation-in-part of PCT/DK96/00034 Jan. 22, 1996.

[51] Int. Cl.$^6$ .................................................. A61M 15/00
[52] U.S. Cl. ........................ 128/203.15; 128/203.23; 128/203.12
[58] Field of Search .......................... 128/207.14, 911, 128/912, 203.12, 203.15, 203.23; 604/24, 26, 37, 58, 59, 60, 142, 117

[56] References Cited

U.S. PATENT DOCUMENTS

| | | | |
|---|---|---|---|
| 32,789 | 7/1861 | Segnitz | 604/58 |
| 39,678 | 8/1863 | Russell | 604/58 |
| 391,546 | 10/1888 | Mess | 128/203.12 |
| 1,586,716 | 6/1926 | Snow | 604/58 |
| 1,824,808 | 9/1931 | Findley | 604/58 |
| 1,827,463 | 10/1931 | Davis | 604/58 |
| 2,223,611 | 12/1940 | Gross | 604/58 |
| 2,470,297 | 5/1949 | Fields | 604/58 |
| 4,117,844 | 10/1978 | James | 128/266 |
| 4,265,236 | 5/1981 | Pacella | 128/203.23 |
| 4,524,769 | 6/1985 | Wetterlin | |
| 4,593,690 | 6/1986 | Sheridan et al. | 128/207.15 |
| 4,907,583 | 3/1990 | Wetterlin et al. | |
| 5,033,463 | 7/1991 | Cocozza | 128/203.12 |
| 5,287,850 | 2/1994 | Haber et al. | 128/203.21 |
| 5,357,945 | 10/1994 | Messina | 128/203.12 |

FOREIGN PATENT DOCUMENTS

| | | |
|---|---|---|
| 28 15 039 | 12/1978 | Germany . |
| WO 90/87351 | 7/1990 | WIPO . |

*Primary Examiner*—Aaron J. Lewis
*Assistant Examiner*—William J. Deane, Jr.
*Attorney, Agent, or Firm*—Merchant Gould Smith Edell Welter and Schmidt

[57] ABSTRACT

An inhaler comprises a tubular body in which an air flow passage is defined. A single dose of an active, inhalable, particulate substance is arranged within the air flow passage and is sealed or closed in relation to the ambient atmosphere by closure means, such as removable caps, a section of the flow passage extending from a free mouthpiece end of the tubular body along a major part of the total length of the flow passage is preferable 7-35 mm$^2$, for example about 20 mm$^2$. The inhaler may be adapted to be used only once, and the tubular body of the inhaler may be a length of a simple tube similar to a drinking straw.

44 Claims, 11 Drawing Sheets

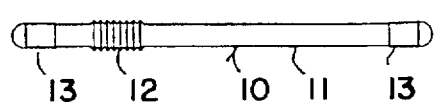
FIG. 1A
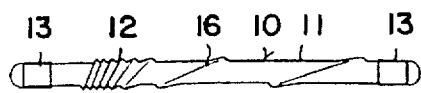
FIG. 2A
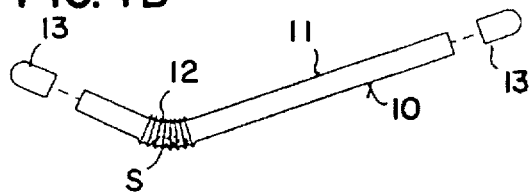
FIG. 1B
FIG. 2B
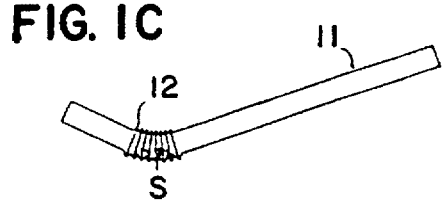
FIG. 1C
FIG. 2C
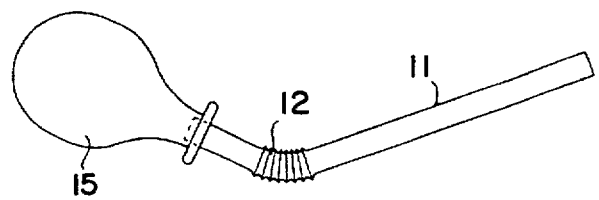
FIG. 1D
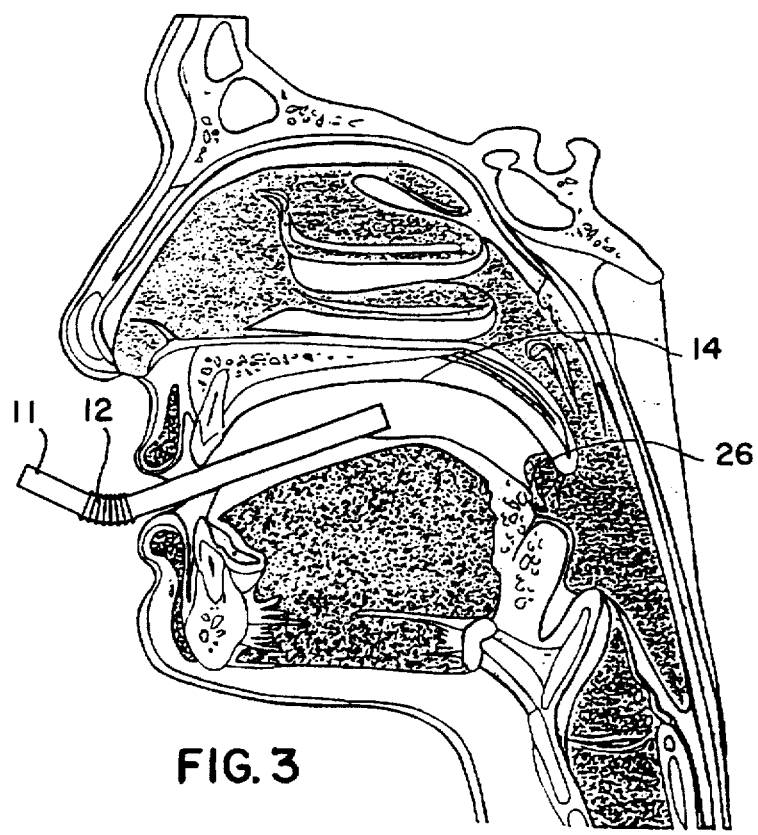
FIG. 3

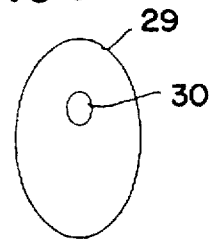
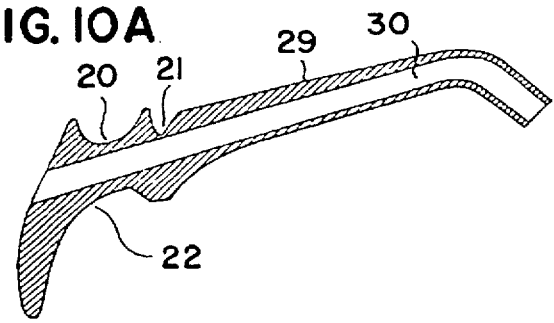
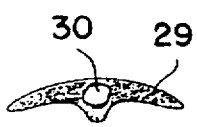
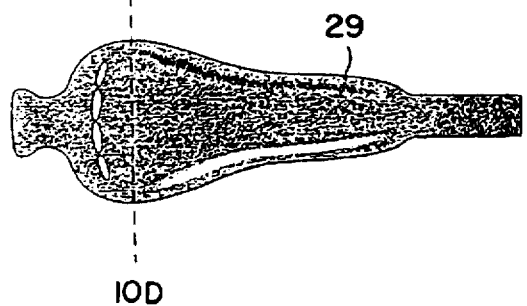
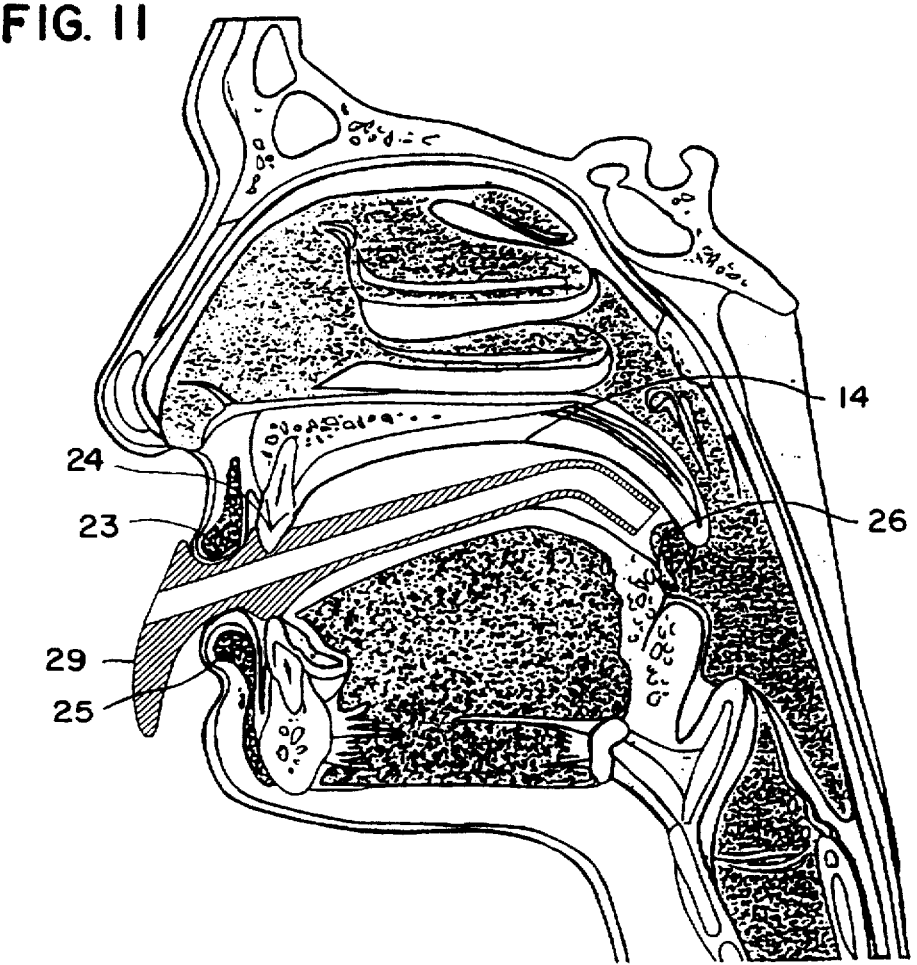

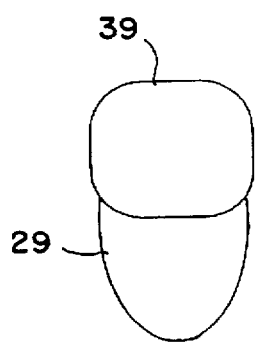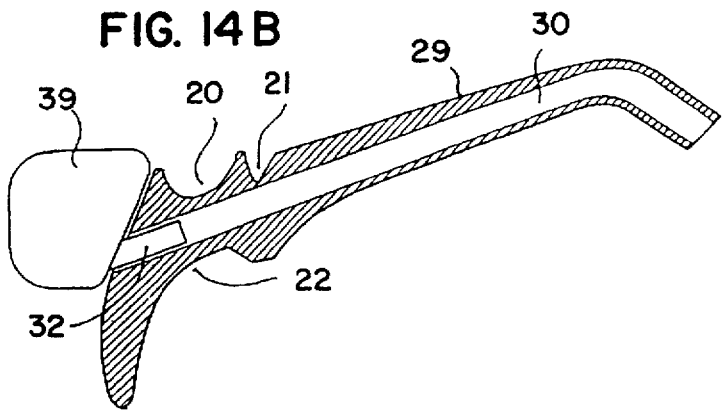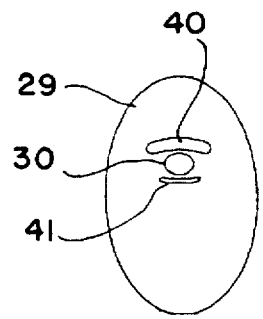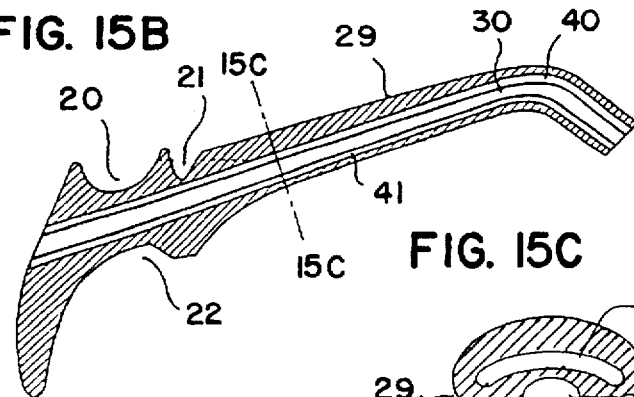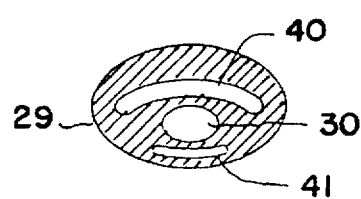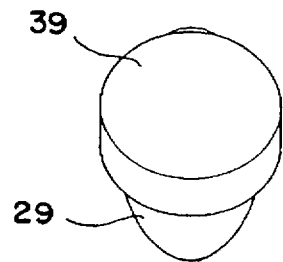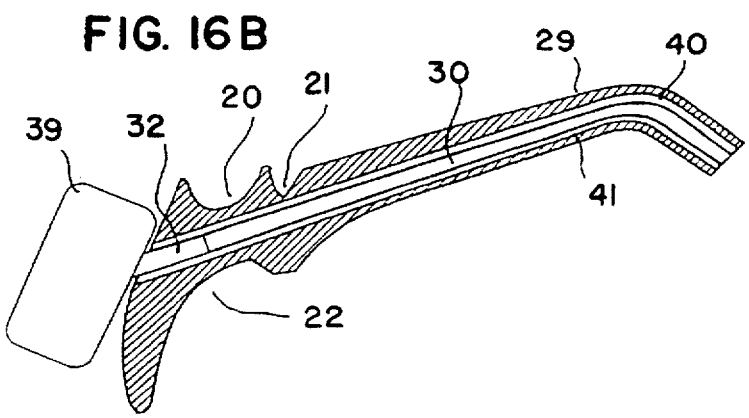

INHALER

This application is a continuation-in-part of PCT/DK96/00034 filed 22 Jan. 1996.

The present invention relates to an inhaler of the type comprising a tubular body defining an air flow passage therein.

Numerous inhalers of this type are known. As examples, U.S. Pat. Nos. 4,524,769 and 4,907,583 and the international application WO 90/07351 disclose inhalers each comprising dosing means for supplying a dose of a particulate active substance to the air flow passage when the inhaler is to be used. The outlet end of the discharge passage is defined by a mouthpiece or nozzle which during use of the inhaler is positioned between the lips of the user. These known inhalers are of a relatively complicated structure, and they are not simple in use because the dosing means has to be operated each time the inhaler is to be used. Furthermore, these known devices are relatively heavy and bulky to carry in a pocket or in a ladies handbag.

When a particulate or powdered substance is inhaled through a mouthpiece or nozzle positioned between the users lips a substantial part of the active substance suspended in the inhaled air flow will not reach the lungs of the user, but may be swallowed or may impinge the mucous membrane of the oral cavity of the user. This does not only mean that a substantial amount of the active substance is lost, but also that the active substance coming into contact with the mucous membrane of the oral cavity or arriving at the stomach may have undesired side effects.

As disclosed in German Offenlegungsschrift No. 2815039 this problem may be solved by using a mouthpiece which in use extends into the oral cavity and along the tongue of the user. When a fluid flow including an active substance is directed into the oral cavity of the patient, for example from an inhaler or an atomizing device connected to the outer end of the mouthpiece, it is possible to direct such fluid flow towards a desired part of the oral cavity, such as the throat or trachea of the patient.

The present invention provides an inhaler which may be produced in a very simple manner and at low cost and which is nevertheless very efficient.

The inhaler according to the invention comprises a tubular body defining an air flow passage therein and is characterized in comprising only a single dose of an active, inhalable, particulate substance arranged within the air flow passage, said dose being sealed or closed in relation to the ambient atmosphere by closure means which are to be removed or opened by a user prior to use, the inhaler being intended to be used only once. Thus, when the inhaler is to be used the closure means have to be removed or opened whereafter the active substance, which is positioned within the air flow passage, may be inhaled by the patient or user in a usual manner.

In the inhaler according to the invention the airflow passage may be without any tortuous sections which may promote precipitation or formation of a coating of the active substance on inner wall surface parts of the flow passage. The build up of such coating is further made unlikely when the inhaler is of a type being used only once. An inhaler which is used only once is much more hygienic than inhalers intended for multiple uses.

The said closure means may be of any suitable type, such as caps, films, or foils which are removably arranged at the opposite ends of the tubular body. Alternatively, the closure means may comprise removable, puncturable or rupturable membranes extending across the air flow passage and being axially spaced therein so that the dose of active substance is arranged therebetween. The closure means could, of course, be of any other type, which is able to seal the dose of active substance in relation to the ambient atmosphere until the inhaler is to be used, and which may be removed or opened by a patient or user prior to use.

According to another aspect the present invention provides an inhaler having a tubular body defining an air flow passage therein and means for supplying a dose of an active, inhalable, particulate substance into the flow passage, and the inhaler according to the invention is characterized in that the cross-sectional area of the flow passage does not exceed 75 mm$^2$ along the length of a flow passage section extending from a free mouthpiece end of the tubular body along a major part of the total length of the flow passage.

when such an inhaler is to be used by a patient a dose of an active substance is supplied into the flow passage by operating the supply means. The patient may now inhale the active substance by inserting the mouthpiece end between the lips and by forcefully inhaling air through the air flow passage defined in the inhaler. Because the cross-sectional area of the inner section of the air flow passage is relatively small, the air velocity in this section will be relatively high. Such high air velocity promotes atomization of the dose of particulate active substance and suspension of the finely divided particles in the air flow.

Also, when the inhaler has a single dose of active substance arranged within the air flow passage and is intended for single use only as described above, the cross-sectional area of the flow passage preferably does not exceed 75 mm$^2$ along the length of the flow passage section extending from a free mouthpiece of the tubular body along a major part of the total length of the flow passage.

In order to obtain a high air flow rate the cross-sectional area of the said flow passage section preferably does not exceed 70 mm$^2$ and is more preferably less than 50 mm. In the presently preferred embodiments the cross-sectional area of the flow passage section is 7–35 mm$^2$ and preferably about 20 mm$^2$.

The means for supplying a dose of an active substance into the flow passage may be of any known type to which doses of an active particulate substance may be fed in the form of small ampoules containing a single dose, or replaceable cartridges containing several doses. Alternatively, the inhaler may be adapted to be used only a few times or only once, and in such case the substance supply means may form a unitary part of the inhaler. As an example, the substance supply means may comprise one or a few dose containing chambers or pockets defined in the walls of the tubular body defining the air flow passage. Each dose containing chamber may be separated from the adjacent part of the flow passage by a film, membrane, or a wall part which may be punctured or ruptured by the user, for example by applying an inwardly directed pressure to the outer surface of the tubular body at the respective position.

The flow passage or the flow passage section may have any cross-sectional shape, such as square, rectangular, polygonal, elliptical, or circular. Furthermore, the cross-sectional area of the flow passage or the flow passage section may vary along the length thereof. Thus, the cross-sectional area of the flow passage or flow passage section may be smaller at the mouth piece end than at the opposite end of the flow passage. In the preferred embodiment, however, the flow passage or flow passage section has a substantially circular cross-section, the inner diameter of the flow passage section, which may be the total length of the air flow passage, being substantially the same along the length of the section. Thus, in a very simple embodiment the inhaler is formed similar to a drinking straw.

The tubular body of the inhaler and the air flow passage defined therein may have any suitable shape. Thus, the flow passage may have any suitable rectilinear, zigzag, angular or curved course or any combination of such courses. Preferably, the flow passage comprises a curved section. As an example, the flow passage may comprise one or more pairs of substantially rectilinear sections and intermediate curved sections.

The tubular body of the inhaler may have a predetermined, permanent shape which cannot be changed by the user. In a preferred embodiment the tubular body comprises at least one bendable section so that the shape of the tubular body may be adapted to the form of the oral cavity of the individual user. The walls of the tubular body forming the bendable section may be made from a deformable plastic material. Alternatively, the flexibility of the bendable section may be obtained by providing the bendable section of the tubular body with peripherally extending corrugations. The bottoms of these corrugations may be provided with codes, such as colours, numbers, letters, or other kinds of indications, for assisting in obtaining a bend suitable for the individual user. When a patient or user has determined a shape of the tubular body which has been adapted to his individual oral cavity, the user may read and note the visible code combination. When the user knows his individual code combination he may quickly adjust the bendable section of the tubular inhaler body next time he is using an inhaler of the same type.

In order to improve the dispersion of the particulate active substance in the air flowing through the air flow passage the inhaler may further comprise means for imparting a rotational movement to the air about the longitudinal axis of the flow passage. Such means may, for example, be helical grooves or ribs formed on the wall surface parts of the tubular body defining the flow passage, or rotation imparting members arranged centrally within the air flow passage.

The tubular body of the inhaler may comprise a mouth piece section of any suitable length extending during use from the teeth of the user to any desired position within the oral cavity of the user. Thus, by suitably adapting the length and the shape of the mouthpiece section the inner end of the air flow passage may be positioned adjacent to and may be directed towards any part of the oral cavity which is to be treated by means of the active particulate substance. In cases where the active substance is to be inhaled to the lungs or bronchial tubes of the user or patient, for example when the active substance is a medicament for alleviating asthmatic deceases, the mouthpiece section of the tubular body preferably has a length so as to extend during use from the teeth of the user to a position adjacent to the root of the user's tongue. The mouthpiece section may then advantageously be shaped so that the inner end of the air flow passage is directed towards the throat or trachea inlet of the patient or user. Thereby it may be secured that substantially all of the active substance of the dose positioned in or supplied to the air flow passage will reach its target area.

In order to secure that the inhaler is correctly positioned within the oral cavity of the user or patient the inhaler may further comprise a bite piece formed on the outer surface of the tubular body for engaging with the upper jaw teeth of the user. Such bite piece may form an integral part of the tubular body. It is preferred, however, that the shape of the bite piece is adapted to the teeth of the individual user. In such case the relatively expensive and individually formed bite piece is removably mounted on the tubular body of the inhaler so that the bite piece may be kept and reused when the tubular body is discarded. Such removably mounted bite piece may advantageously be used in connection with tubular bodies adapted to be used only a few times or only once. The bite piece may be combined with a set of false teeth. Thus, such a set of false teeth may comprise means for positioning the tubular body in relation to the oral cavity of the user, or the bite piece may be individually shaped when the false teeth are made to the individual user.

The tubular body of the inhaler may have a fixed length. Alternatively, the tubular body may be movable from a retracted storage condition to an extended condition of use. This may, for example, be obtained by providing the tubular body with peripheral corrugations along a major part of its length so as to allow longitudinal stretching of the tubular body. As another possibility, the tubular body may comprise telescopically cooperating tubular parts allowing such parts to be moved between retracted and extended positions. The closure means sealing the dose of active substance in relation to the ambient atmosphere or the supply means for supplying such dose into the air flow passage of the inhaler may be opened or actuated automatically when the tubular body is moved from its retracted storage condition to its extended is condition of use.

In order to completely eliminate the risk that larger particles of the active substance or of foreign matter, such as ruptured or removed closing means, are inhaled by a patient the inhaler may further comprise retaining means arranged within the flow passage for retaining particles of a size exceeding a predetermined size. Such retaining means may, for example, comprise a sieve or screen extending across the flow passage and being arranged downstream of the dose of active substance to be inhaled. Alternatively, when the closure means comprise removable closure caps, such caps may be integrally connected to the tubular body by flexible strings or bands. Alternatively or additionally, the free end portions of the tubular body may be bent towards each other so as to position the free ends closely adjacent, and the free ends may then be closed by a common, removable closure member, such as a pair of interconnected or integrally formed closure caps. Furthermore, at least one of the cap members is preferably made from a transparent material, or the tubular body is at least partly made from a transparent material, so that the patient or user may see that the tubular body contains a dose of the active substance.

In most cases the patient or user is able to inhale atmospheric air through the air flow passage so as to obtain an air flow being sufficiently vigorous to suspend the active substance therein in an atomized condition. However, smaller children and adult persons having a substantially reduced lung capacity may not be able to generate a sufficient air flow rate through the air flow passage. Therefore, the inhaler may further comprise forced flow generating means for providing a forced air flow through the flow passage. Such flow generating means may be of any kind which is able to generate pressurized air. As an example, the forced flow generating means may comprise a compressible bulb to be mounted on the outer end or air inlet end of the tubular body. The flow generating means may then be actuated at the same time as the patient is inhaling.

It should be understood that the inhaler according to the present invention should not necessarily be inserted into the oral cavity of the user, and the term "mouthpiece" is not intended to indicate that it should necessarily be inserted into the user's mouth. Thus, one end or the mouthpiece end of the tubular body may be adapted to be inserted into a nostril of a user or patient. In such case, the inhaler preferably comprises a pair of tubular bodies and a connecting part for interconnecting the same, said one end or mouthpiece end of said pair of tubular bodies being arranged in spaced relationship, so that said ends may be inserted into the nostrils of a user or patient.

The invention further provides substance supply means for use in connection with an inhaler of the type described above including such supply means, said supply means comprising a tube length containing only a single dose of a particulate active substance, said dose being sealed or closed in relation to the ambient atmosphere by closure means which are to be removed or opened by a user prior to use, one end of the tubular length being insertable in or connectable to the air flow passage of the inhaler. The tube length which forms a capsule for the active substance is preferably bendable, for example due to a plurality of adjacent peripherally extending corrugations. The tube length may be closed at opposite ends by means of removable closure caps. The free ends of the tube length may be bent together and be closed by a common closure member or interconnected closure caps.

The invention will now be further described with reference to the drawings, wherein FIG. 1 illustrates a first embodiment of the inhaler according to the invention, FIG. 2 illustrates a second embodiment of the inhaler according to the invention, FIG. 3 illustrates the use of the inhaler shown in FIG. 1, FIG. 4 illustrates a third embodiment of the inhaler according to the invention, FIG. 5 illustrates a fourth embodiment of the inhaler according to the invention, FIG. 6 illustrates how the inhaler shown in FIG. 5 may be used, FIG. 7 illustrates how a bent portion of the inhaler shown in FIG. 6 may be provided with bending codes, FIG. 8 illustrates a fifth embodiment of the inhaler according to the invention, FIG. 9 illustrates how the inhaler shown in FIG. 8 may be used, FIG. 10 illustrates a mouthpiece for a sixth embodiment of the inhaler according to the invention, FIG. 11 illustrates how the mouthpiece shown in FIG. 10 may be positioned in the oral cavity of the user, FIGS. 12 and 13 illustrate in an enlarged scale two different devices for supplying separate doses of active substance to the flow passage of the mouthpiece shown in FIGS. 10 and 11, FIG. 14 illustrates the mouthpiece shown in FIG. 10 provided with a third device for supplying doses of active substance, FIG. 15 illustrates a further embodiment of a mouthpiece for use in connection with the inhaler according to the invention, FIG. 16 illustrates the mouthpieces shown in FIG. 15 provided with a device for supplying active substance thereto, FIG. 17 illustrates the function of the inhaler shown in FIGS. 15 and 16, FIG. 18 illustrates a seventh embodiment of the inhaler according to the invention, FIG. 19 illustrates an eighth embodiment of the inhaler according to the invention, FIG. 20. illustrates how the inhaler shown in FIG. 19 may be used, FIG. 21 shows a capsule containing a single dose of an active substance, FIG. 22 illustrates how the capsule shown in FIG. 21 may be used in connection with a mouthpiece as shown in FIGS. 14–16

Figure 4A:
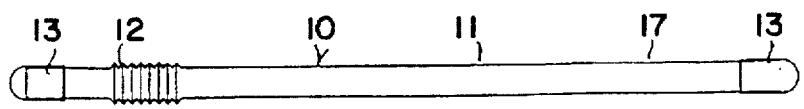

FIG. 1 shows an inhaler 10. When delivered from the manufacturer, the inhaler may comprise a straight, thin-walled tubular body 11 having a bendable section 12 and removable caps 13 closing the opposite open ends of the tubular body 11. The inner bore of the tubular body 11 which defines an air flow passage of the inhaler contains a single dose of a particulate or powdered active substance, such as steroids, $\beta_2$-agonists, anticholinergica, or other medical products. The tubular body 11 may have a circular cross-sectional shape and have a substantially uniform inner diameter and wall thickness along the length of the tubular body and may be similar to a drinking straw. The section 12 may have peripheral corrugations so as to be bendable. The tubular body 11 may, for example, be made from a suitable plastic material by extrusion, and the inner diameter of the tubular body is preferably within the range of 4–8 mm, for example 5–6 mm. The material of the tubular body 11 may have been treated so as to reduce or eliminate the possibility of static electricity.

The inhaler 10 shown in FIG. 1a which contains only a single dose of the active substances is intended to be used only once whereafter the inhaler is discarded. A suitable small number of disposable inhalers of this type may be packed, for example similar to cigarettes, and they may be carried by the user in a pocket or a ladies handbag without occupying much space.

When an inhaler 10 of the type shown in FIG. 1a is to be used the user or patient may shake the inhaler so as to disintegrate the particulate active substances contained therein. The bendable section 12 may now be bent whereby the active substance S is positioned within the corrugation troughs of the bendable section 12 as indicated in FIGS. 1a and 1b. Thereafter the caps 13 may be removed as shown in FIG. 1b. The inhaler 10 is then ready for use, and a longer straight end portion of the tubular body may be inserted into the oral cavity 14 of a user or patient as shown in FIG. 3. Because the tubular body 11 has been bent the active substance S contained in the corrugation troughs of the section 12 may be prevented from falling out from the tubular body.

As shown in FIG. 3 the inner end of the inhaler is positioned adjacent to the root of the patient's tongue. When the patient inhales air through the air flow passage defined within the tubular body 11 the particulate active substance S is withdrawn from the corrugation troughs of the section 12 and is suspended in the air flow which is inhaled into the patient's lungs. In case the patient is a small child or for some other reason is not able to inhale sufficiently vigorously a compressible bulb 15 or other means for generating a forced flow through the tubular body 11 may be mounted on the outer end thereof as shown in FIG. 1d. A flow of air with active substance suspended therein may then be blown into the oral cavity 14 at the same time as when the patient inhales.

The embodiment shown in FIG. 2 is slightly modified in relation to the embodiment shown in FIG. 1. Thus, in FIG.

2 the tubular body 11 is provided with a helically extending corrugation 16 which may impart a rotational movement to the air flow being inhaled through the air flow passage defined in the tubular body 11. The tubular body 11 and/or at least one of the closure caps 13 is preferably made from a transparent material so that the user may visually make sure that the inhaler contains a dose of an active substance.

Figure 4B:
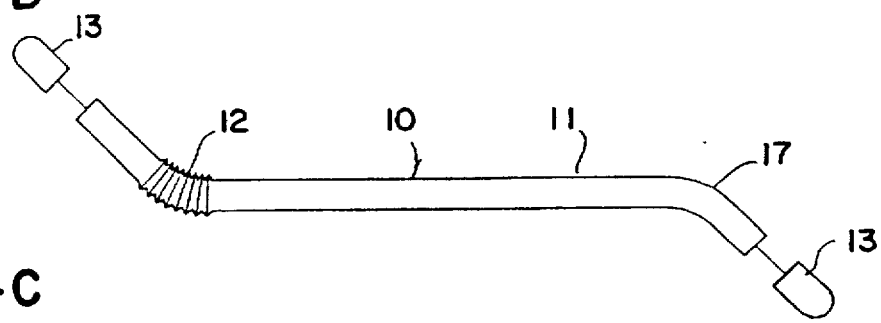
Figure 4C:
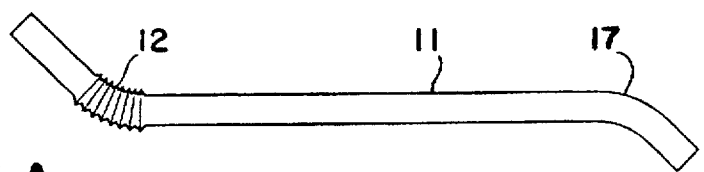
Figure 5A:
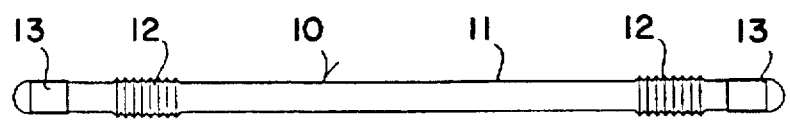
Figure 5B:
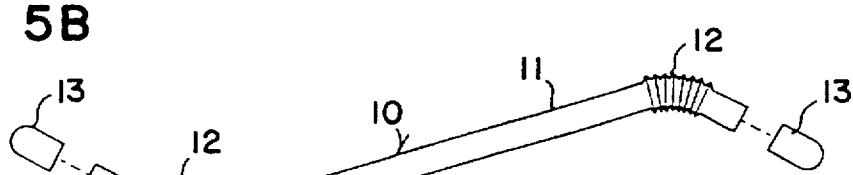
Figure 5C:
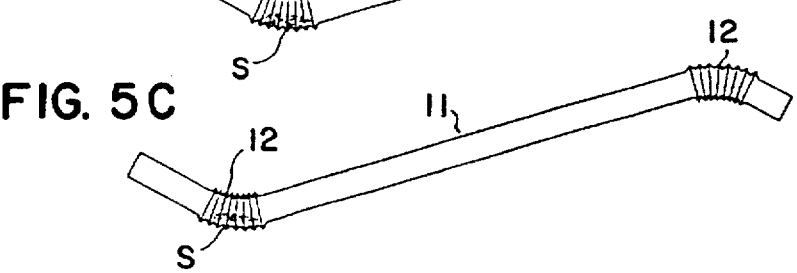
Figure 5D:
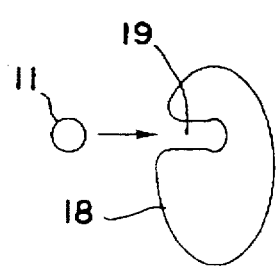
Figure 5E:
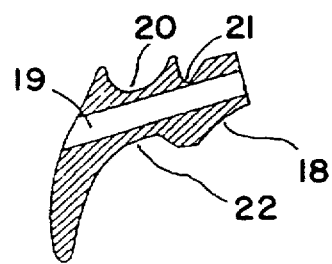

FIG. 4 shows an embodiment 10 having not only a bendable section 12 provided with peripherally extending corrugations, but also a bendable section 17 without such corrugations at an opposite end portion of the tubular body 11. In fact, the material and the wall thickness of the tubular body 11 may be chosen so that any part of the tubular body may be bent into a desired shape. The inhaler shown in FIG. 5 corresponds to that shown in FIG. 4. The only difference is that the embodiment shown in FIG. 5 comprises a bendable section 12 at opposite end portions of the tubular body, which sections 12 both comprise peripherally extending corrugations.

Figure 6:
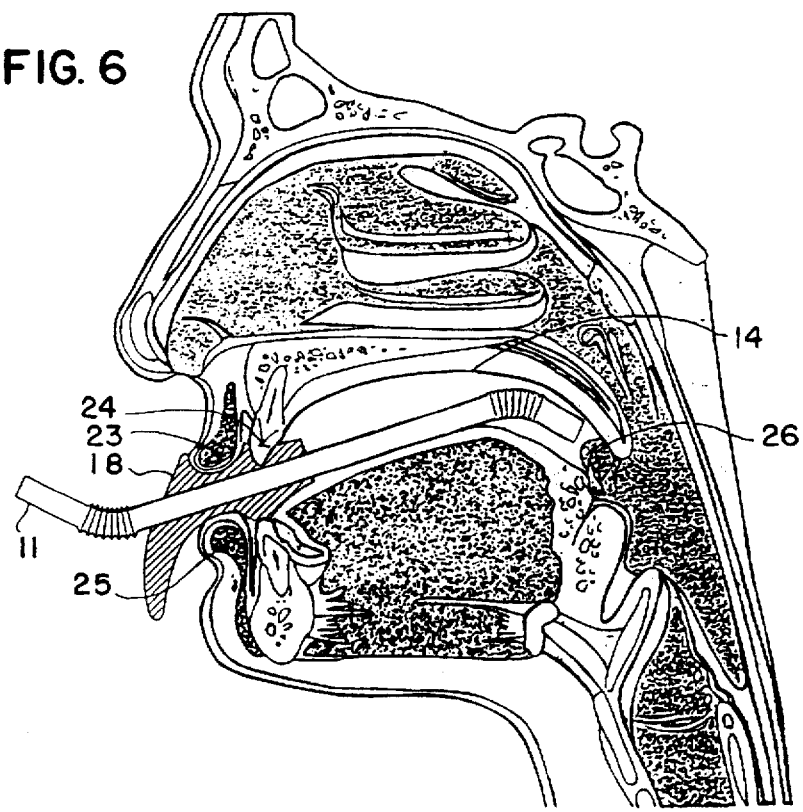

For some patients who are not sensing so well it may be difficult to immediately position the inhalers shown in FIGS. 1, 2, 4, and 5 correctly in the oral cavity 14. Therefore, the tubular body 11 may advantageously be inserted in a bite piece or teeth block 18 of the type shown in FIG. 5. FIG 5d is an end view of the bite piece 18, while FIG. 5e is a longitudinally sectional view of the bite piece. The bite piece 18 comprises a longitudinally extending channel or slot 19 which is dimensioned so that the tubular body 11 may be snugly received therein as indicated by an arrow in FIG. 5d. Troughs or grooves 20 and 21 are defined in the upper outer surface of the bite piece 18, and a trough 22 is defined in the lower outer surface of the bite piece. When the bite piece or teeth block 18 has been mounted on the tubular body 11 which has been bent into the desired shape and the closure caps 13 have been removed as explained above, the inhaler assembly comprising the tubular body 11 and the bite piece 18 may be inserted into the user's mouth. As shown in FIG. 6 the bite piece or teeth block 18 may then be positioned so that the upper lip 23 and the upper teeth 24 of the patient are positioned in the troughs 20 and 21, respectively, while the lower lip 25 of the user is positioned in the trough 22 of the bite piece or teeth block 18 whereby the tubular body 11 may be positioned very accurately within the user's oral cavity 14.

As shown in FIG. 6 the inner end portion of the tubular body 1i may be shaped so that the inner open end of the tubular body is positioned adjacent to and directed towards the throat 26 of the user or patient. Thus, almost all of the active substance contained within the tubular body may be transferred to the patient's lungs when the patient vigorously inhales air through the air flow passage defined within the tubular body 11. It should be understood that the inner end portion of the tubular body 11 could be directed towards any desired surface part of the oral cavity to be treated by the active substance contained in the inhaler.

Figure 7A:
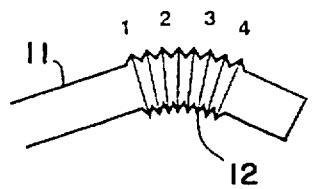

In order to ensure that the open inner end of the tubular body 11 is directed towards the throat 26 of the patient or user as shown in FIG. 6, or towards any other surface part of the oral cavity 14 to be treated it is important that the shape of the inner end of the tubular body 11 is adapted to each individual user. When the inner end of the tubular body has a bendable section 12 provided with peripherally extending corrugations, the bend or curvature which is adapted to the oral cavity of a specific patient or user may be expressed as a code which may be remembered. FIG. 7 illustrates examples of such coding. As indicated in FIG. 7a a number may be assigned to each or every second of the peripheral troughs formed between the adjacent peripheral corrugations of the bendable section 12. The number code to be remembered by the user may then indicate which of the upwardly facing trough-parts should be fully opened and which should not.

Figure 7B:
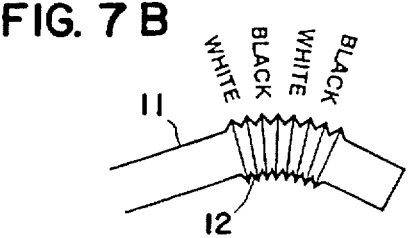
Figure 7C:
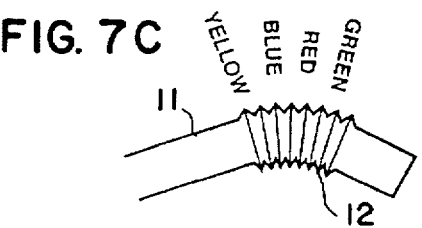
Figure 8A:
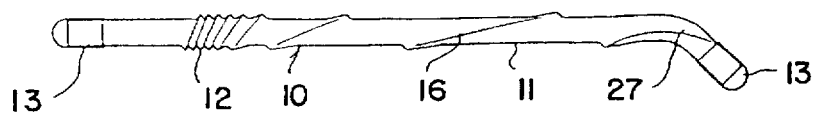
Figure 8B:
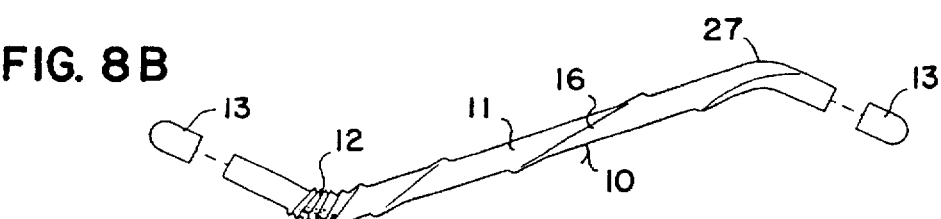
Figure 8C:
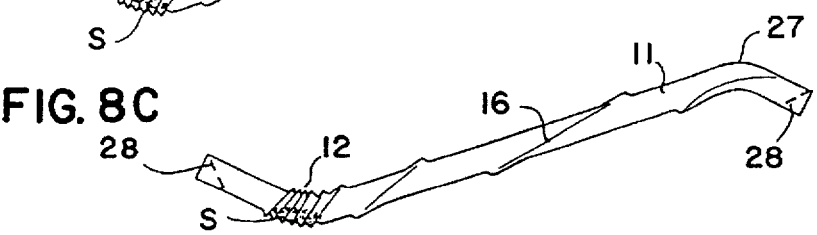
Figure 8D:
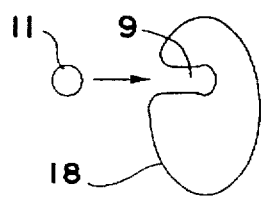
Figure 8E:
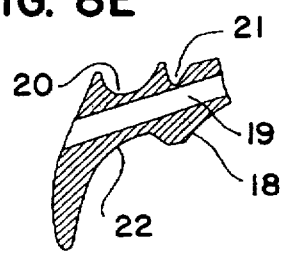

Alternatively, adjacent troughs may be differently coloured or different colours may otherwise be assigned to the various troughs as indicated in FIGS. 7b and 7c. The bend or curvature suitable for each individual user or patient may then be expressed as a colour code in a similar manner as explained above in connection with the number coding.

The inhaler 10 illustrated in FIG. 8 is of the same type as that described above with reference to FIG. 2. However, the inner end portion of the tubular body 11 shown in FIG. 8 has a permanent bend 27 which is made when the inhaler is being manufactured.

Like in the inhaler shown in FIG. 2 the tubular body 11 has a helical corrugation 16 extending along the length of the tubular body. As explained above in connection with FIG. 2, such helical corrugation may tend to impart a rotational movement to air inhaled through the tubular body 11. The tubular body 11 in any of the embodiments shown in FIGS. 1, 2, 4, 5 and 8 may, for example, be made by injection moulding, blow moulding, or extrusion. In the latter case, the corrugations may be formed in the walls of the tubular body 11 during a subsequent manufacturing stage. The tubular bodies 11 shown in FIGS. 2 and 8 may, alternatively, be made by helically winding a strip of sheet material, such as paper, paperboard or another fibrous sheet material, with mutually overlapping adjacent edge portions. Such edge portions may then be interconnected or sealed, whereby the helically extending corrugation 16 may be formed. In order to facilitate mounting of the snugly fitting caps 13 on the opposite ends of the tubular body 11 when a dose of active material has been arranged therein, the tubular bodies 11 illustrated in FIGS. 1, 2, 4, 5, and 8 may be cut on the bias as indicated with dotted lines at 28 in FIG. 8c.

Figure 9:
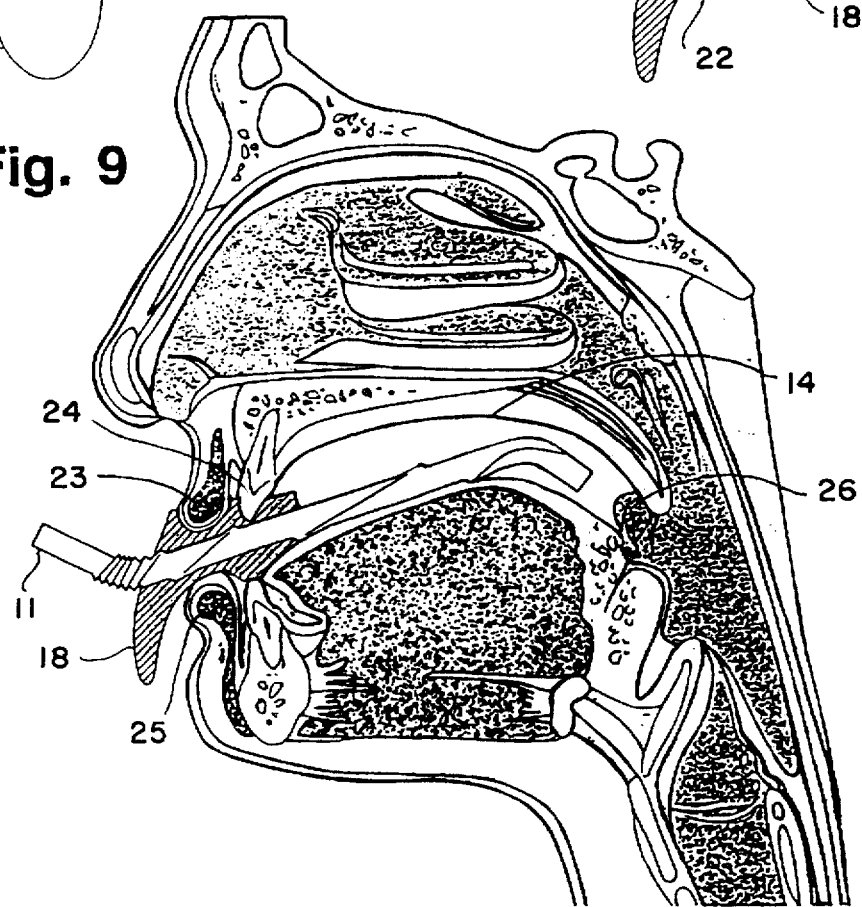

The tubular body 11 shown in FIG. 8 may be inserted into the channel or slot 19 of a bite piece or teeth block 18 as explained above in connection with FIG. 5. Thereafter, when the bendable section 12 has been given the desired shape and the caps 13 have been removed, the inhaler may be positioned in the mouth of a patient as illustrated in FIG. 9 and as explained above in connection with FIG. 6.

FIG. 10 illustrates an embodiment of a tubular body 29 for an inhaler according to the invention. FIGS. 10a, 10b, 10c, and 10d illustrate a longitudinally sectional view, a top plan view, an end view, and a cross-sectional view along the line D—D, respectively. The tubular body 29 defines a longitudinally extending air flow passage 30 having a substantially uniform cross-sectional area along the length thereof. The outer end (the left hand end in FIG. 10) of the tubular body 29 has a shape corresponding to the shape of the bite piece or teeth block 18 shown in FIGS. 5 and 8. This means that in the embodiment shown in FIG. 10 the bite block is formed integrally with the tubular body 29. Thus, the tubular body 29 has troughs or grooves 20 and 21 formed in the upper outer surface of the outer end portion of the tubular body 29. These troughs 20 and 21 are intended to receive the upper lip 23 and the upper teeth 24, respectively, of a user or patient. Furthermore, a trough 22 is formed in the lower outer surface of the tubular body 29 for receiving the lower lip 25 of the user as illustrated in FIG. 11.

The tubular body 29 illustrated in FIG. 10, which is preferably made from plastic by injection moulding, may be adapted to be used only once. In such case, a single dose of an active powdered or particulate material may be arranged within the air flow passage 30, and the open ends of the air flow passage may be sealed or closed by removable sealing or closing means, such as a film or foil which may be torn off. Alternatively, the tubular body 29 illustrated in FIG. 10 may be adapted to cooperate with a dose feeding device for feeding a dose of powdered or particulate active material into the air flow passage 30 when the inhaler is to be used. In that case the tubular body 29 is preferably adapted to be used several times, and each sample may then have a shape which has been adapted to the individual user.

Figure 12:
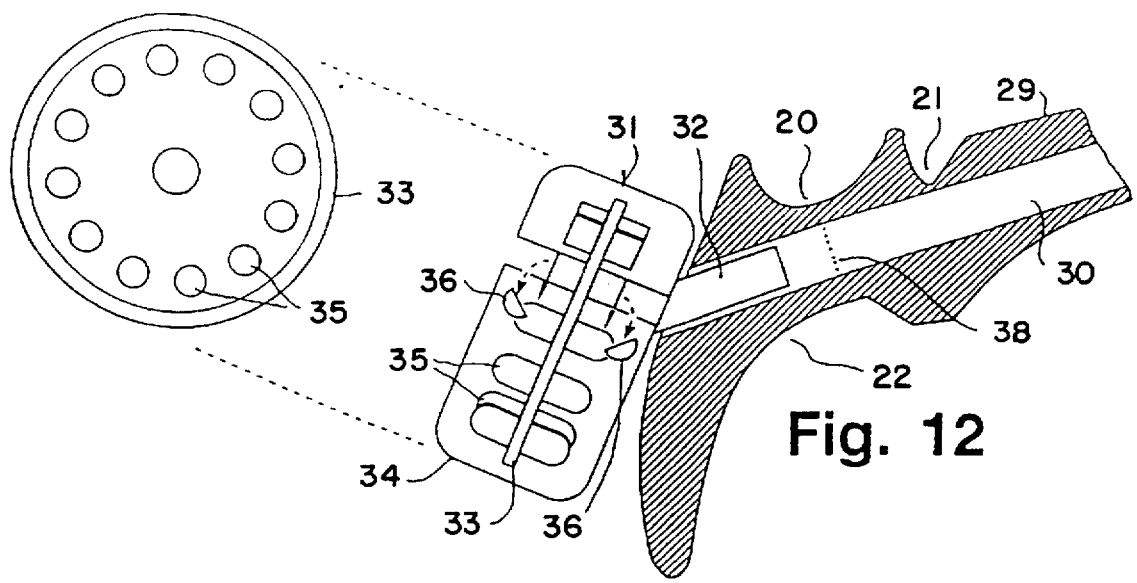
Figure 13:
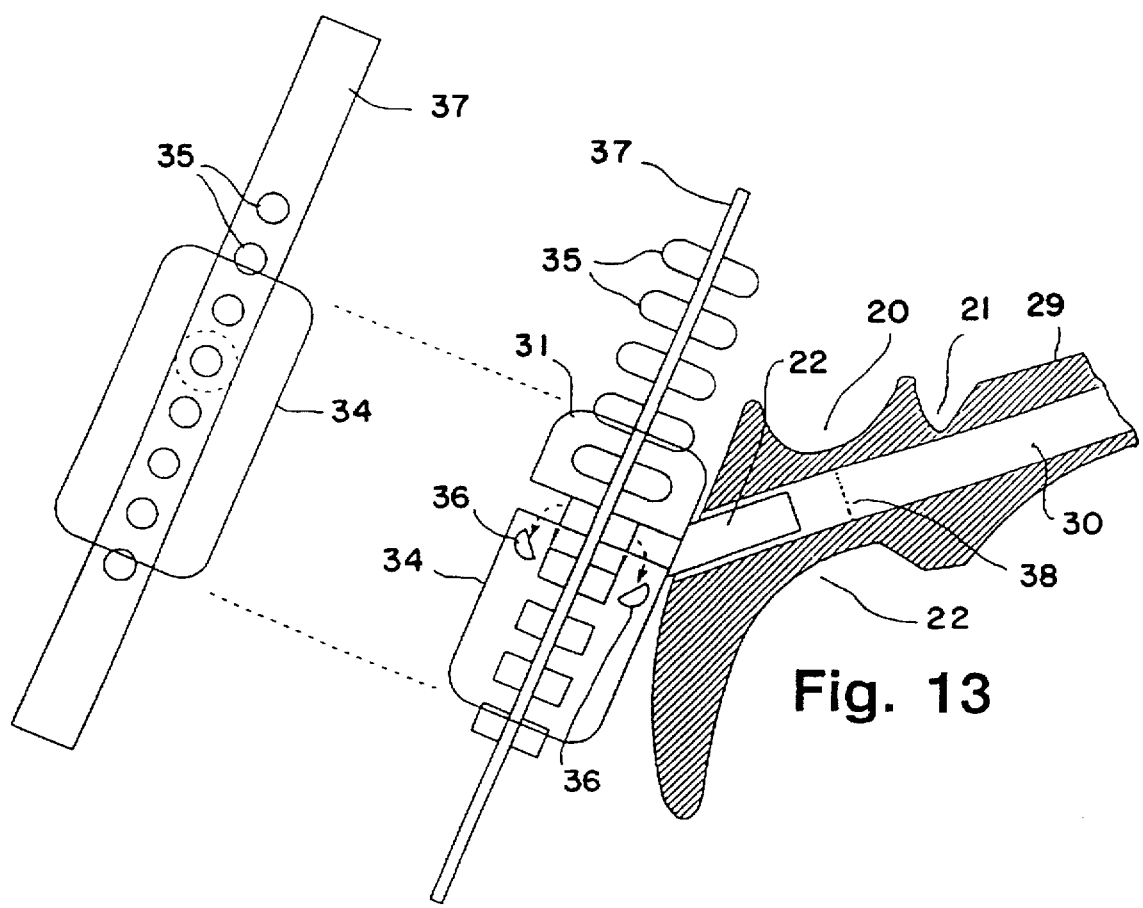

FIGS. 12 and 13 show the outer end portion or bite piece of the tubular body 29 provided with a separate dose feeding device 31. The dose feeding device 31 comprises a short tube section 32 which may be inserted into the air flow passage 30 of the tubular body 29. In FIG. 12 the dose feeding device 31 comprises a disc 33 which is rotatably mounted within a housing 34. The disc 33 comprises a plurality of capsules 35 in a circular arrangement. The capsules 35 of the disc 33 may successively be indexed to a position of use. By operating parts of the housing 34 the opposite ends 36 of the capsule 35 in this position are cut off whereby the remaining tubular part of the capsule is brought into communication with the tube section 32 and the air flow passage 30 defined in the tubular body 29. The dose of active substance contained in the capsule being cut may now be inhaled when the tubular body 29 has been inserted into the oral cavity of a patient as illustrated in FIG. 11.

The dose feeding device 31 illustrated in FIG. 13 is similar to that illustrated in FIG. 12. In FIG. 13, however, the capsule carrying disc 33 has been replaced by a strip 37 carrying a plurality of capsules 35 arranged in a rectilinear row. In other respects, the dose feeding device 31 of FIG. 13 functions substantially in the same manner as the feeding device shown in FIG. 12. In order to prevent inhalation of the cut capsule ends 36 or other foreign matter, a sieve or grid 38 allowing the particulate active substance, but not the capsule ends 36, to pass may be arranged within the air flow passage 30 as indicated in FIGS. 12 and 13.

FIG. 14 illustrates an embodiment of the inhaler according to the invention comprising a tubular body 29 as that illustrated in FIG. 10. The inhaler further comprises a small container or capsule 39 which may contain a single dose of a particulate or pulverulent active substance. FIG. 14a is an end view of the inhaler, while FIG. 14b illustrates the inhaler in a side view and partially sectional view. The capsule 39 comprises a tube stub or tube section 32 which may be inserted into the outer end of the air flow passage 30, which means that the capsule 39 is replaceable. When the inhaler is to be used closure means (not shown) of the capsule 39 may be removed or ruptured to allow air to flow through the capsule and into the air flow passage 30. As an example, such closure means may comprise a removable cap or a film for closing the tube stub 32 and a removable film or foil closing an opening in the capsule 39, or a removable wall part of the capsule. The capsule or container 39 may then be disposed of when it has been used a single time while the tubular body 29 may be used several times.

FIG. 15 illustrates an alternative embodiment of the tubular body shown in FIG. 14. FIGS. 15a, 15b, and 15c are an end view, a longitudinally sectional view, and a cross-sectional view along the line C—C, respectively. It should be noted that FIG. 15c has been shown in a larger scale than FIGS. 15a and 15b. In addition to the air flow passage 30 the tubular body 29 shown in FIG. 15 comprises longitudinally extending, through-going upper and lower air passages 40 and 41, respectively. When the tubular body 29 is being used and a flow of air with active substance dispersed therein is being inhaled through the air flow passage 30, flows of "false air" are simultaneously being inhaled through the air passages 40 and 41. These flows of false air envelope the air flow in which the active substance is dispersed so as to direct the dispersed active substance in the desired direction and so as to reduce loss of active substance.

FIG. 16 illustrates an inhaler embodiment comprising a tubular body 29 as that shown in FIG. 15 and a replaceable container or capsule 39 of the type which is shown in FIG. 14 and which is replaceably mounted on the tubular body 29 by means of a tube stub 32. The capsule 39 is shaped so that it does not close the inlet openings of the air passages 40 and 41. FIG. 16a is an end view of the inhaler while FIG. 16b is a side view and partially sectional view of the inhaler. Apart from the enveloping air flowing through the air passages 40 and 41 the inhaler illustrated in FIG. 16 may be operated and may function substantially as described above with reference to FIGS. 14 and 15.

Figure 17:
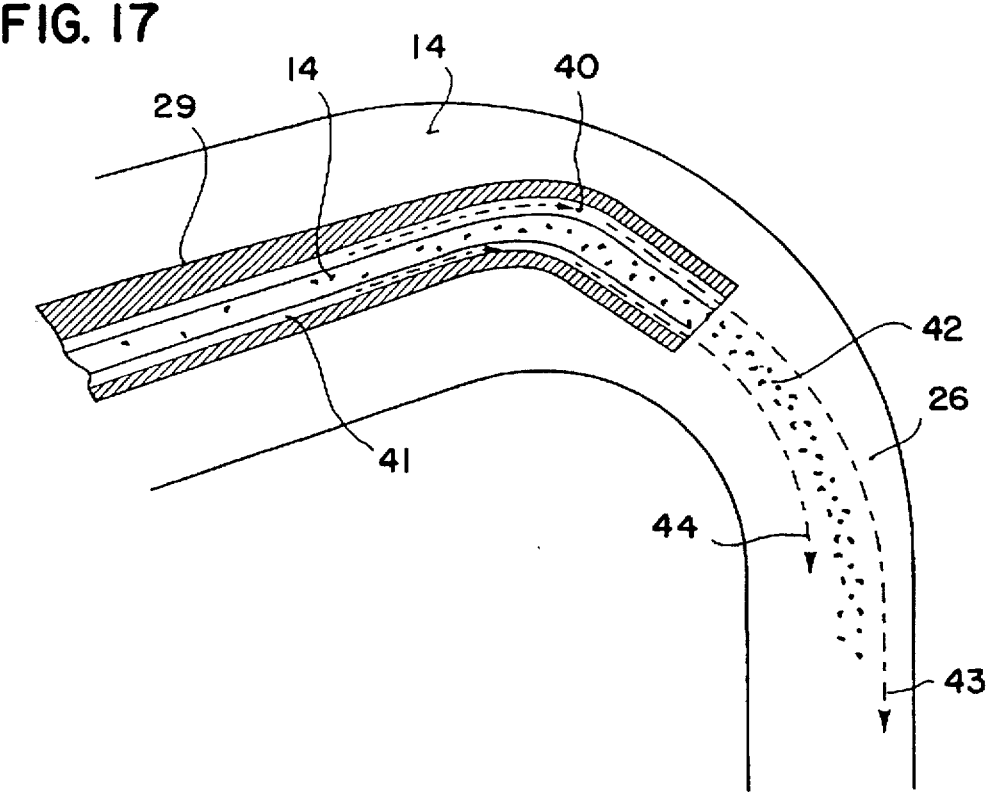

FIG. 17 diagrammatically illustrates the inner end of the inhaler shown in FIG. 16 which has been inserted into the oral cavity 14 of a user or patient. When the patient inhales air through the inhaler an air flow 42 with active substance dispersed therein will be enveloped by flows of atmospheric air which are represented by arrows 43 and 44 and which contain no or few particles of active substance. Such enveloping air flows may assist in conveying the dispersed active substance into the patient's lungs without any substantial loss of active substance.

Figure 18A:
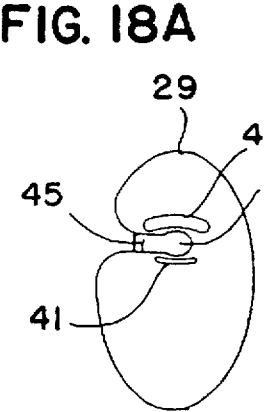
Figure 18B:
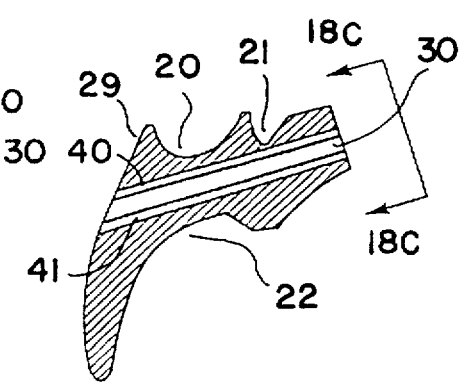
Figure 18C:
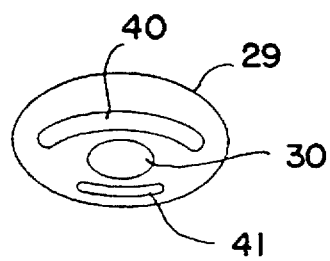

FIG. 18 illustrates a further embodiment of the tubular body 29. FIG. 18a is an end view and FIG. 18b is a longitudinally sectional view of the tubular body 29 while FIG. 18c is an end view in the direction C—C shown in an enlarged scale. The tubular body 29 shown in FIG. 18 is a short version having a shape similar to the outer end portion of the tubular body shown in FIG. 15b at the left hand side of the section line C—C. However, as best illustrated in FIG. 18a the outer end portion of the air flow passage 30 may be in the form of a longitudinally extending channel or groove 45. The tubular body 29 shown in FIG. 18 may be used in connection with a capsule or container 39 as shown in FIGS. 14 and 16, and the tube stub 32 of the capsule 39 may then be received in the channel or groove 45, and the axial length of the channel or groove may correspond to the length of the tube stub or tube section 32 of the capsule 39.

Figure 19A:
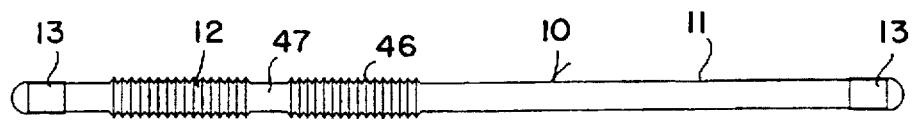
Figure 19B:
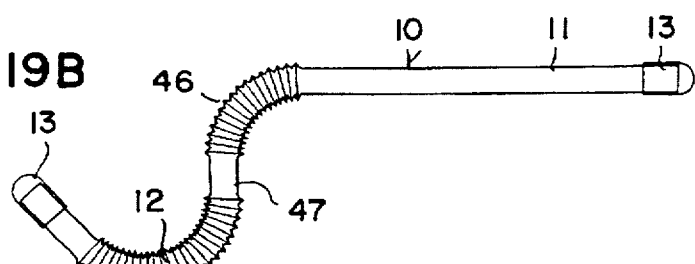
Figure 19C:
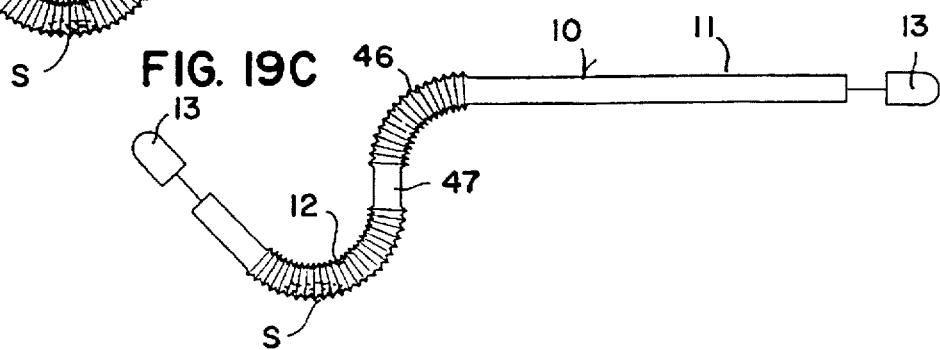
Figure 20:
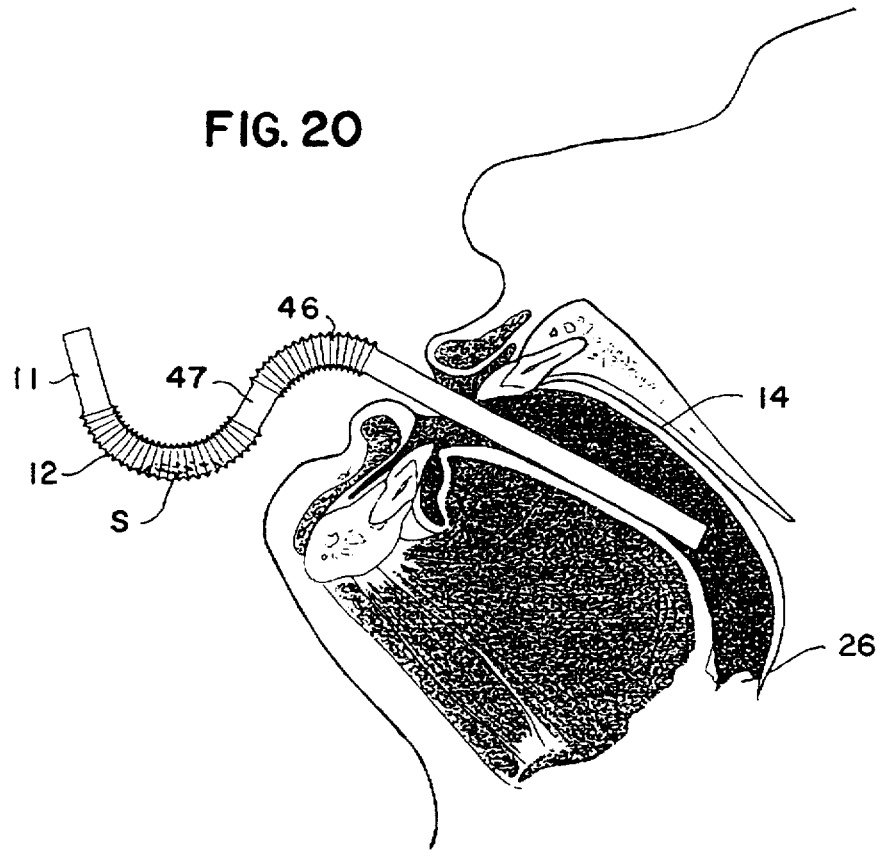

In FIG. 19 an embodiment corresponding to that of FIG. 1 has been shown. However, in addition to the bendable section 12 the tubular body 11 has a second similar bendable section 46 which is spaced from the bendable section 12 by a non-corrugated, rectilinear tubular section 47. The tubular body 11 contains a single dose of an active substance S and when the inhaler 10 is to be used the sections 12 and 46 may be bent as shown in FIGS. 19b and 19c so that the sections 12, 47 and 46 are substantially S-shaped. The active substance S is mainly received in the inner corrugation troughs of the bendable tubular section 12. Now, the removable closure caps 13 may be removed from the opposite ends of the tubular body 11 as illustrated in FIG. 19c, and the tubular body may be inserted into the oral cavity 14 of a user as illustrated in FIG. 20. Even when the user reclines his head as shown in FIG. 20 the active substance S may remain in the inner corrugation troughs of the bendable section 12. When, however, the user or patient inhales air through the air flow passage of the tubular body 11, the velocity of flowing air causes a static pressure drop so that the active substance S is sucked from the corrugation troughs and entrained with and efficiently dispersed in the air flow.

Figure 21A:
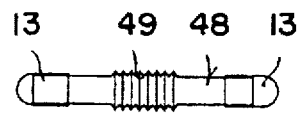
Figure 21B:
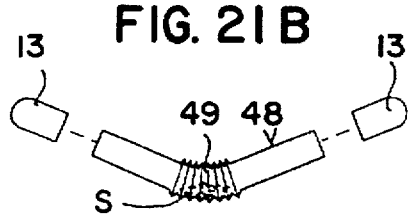
Figure 21C:
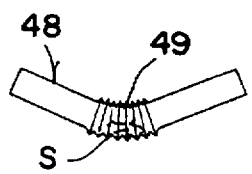
Figure 22A:
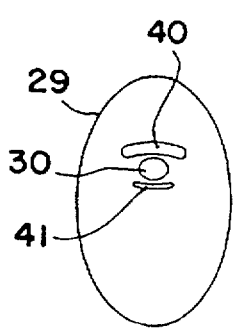
Figure 22B:
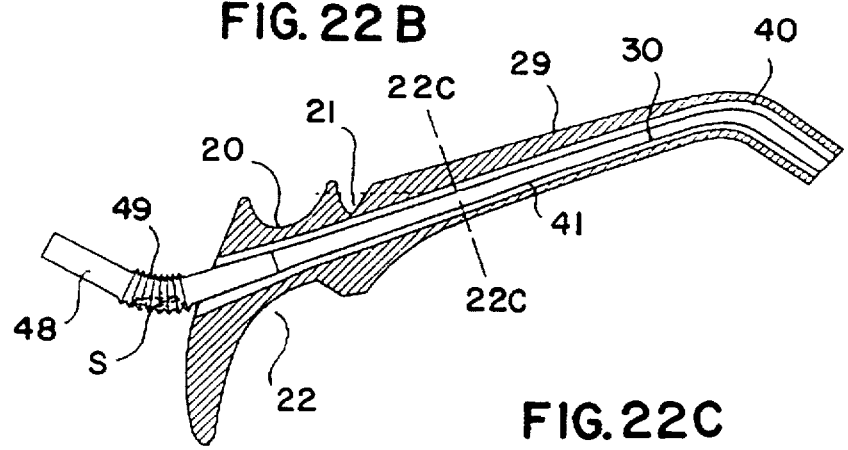
Figure 22C:
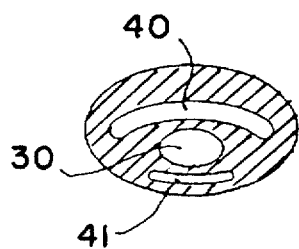

If an inhaler as that shown in FIGS. 1, 2, and 4 is shortened it may be used as a disposable container or capsule for a single dose of an active substance S. Such a tubular container or capsule is shown in FIG. 21 and may be closed at its opposite ends by removable closure caps 13 or by any other removable or breakable closure means. The tubular capsule may have a central bendable section 49 having peripheral corrugations as those previously described. The tubular container or capsule 48 may be used together with any of the tubular bodies 29 shown in FIGS. 10–18. FIG. 22 illustrates how the container or capsule 48 may be used in connection with the tubular body 29 shown in FIGS. 15 and 16. When the tubular capsule 48 is to be used it may be bent as illustrated in FIG. 21b so that the active substance s is collected in the bendable section 49 and is mainly received in the inner corrugation troughs defined therein. When the closure caps 13 have been removed, one end of the capsule 48 may be inserted into the outer end of the air flow passage 30 of the tubular body 29 as illustrated in FIG. 22. Now, the inhaler is ready for use in a manner previously described. When the active substance S from the capsule 48 has been inhaled, the capsule may be discarded and a new capsule is used for the next inhalation.

Figure 23A:
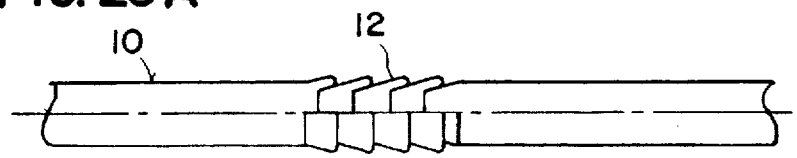
FIG. 23 shows a ninth embodiment of the inhaler.
Figure 23B:
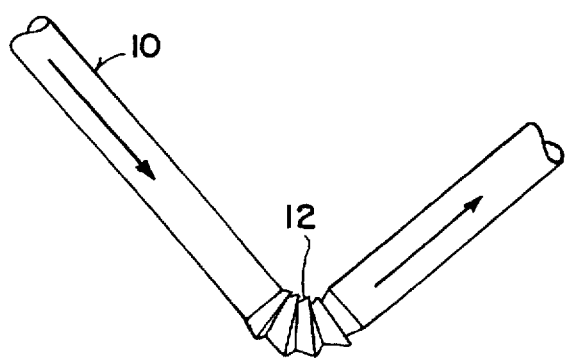
Figure 23C:
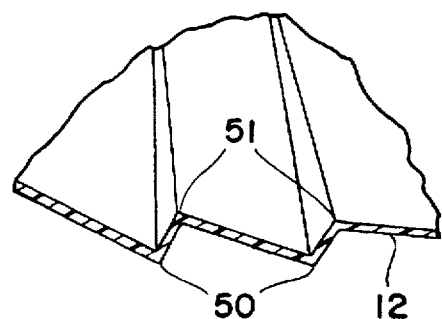

FIG. 23 shows a tubular inhaler 10 in which the section 12 has a number of annular corrugations. FIGS. 23a and 23b illustrate the rectilinear inhaler prior to use and the bent inhaler made ready for use, respectively. As shown in FIG. 23c the corrugations are of a type which is substantially saw tooth shaped in an axial sectional view. Thus, the valleys 50 and peaks 51 of the corrugations are relatively sharp.

Figure 24:
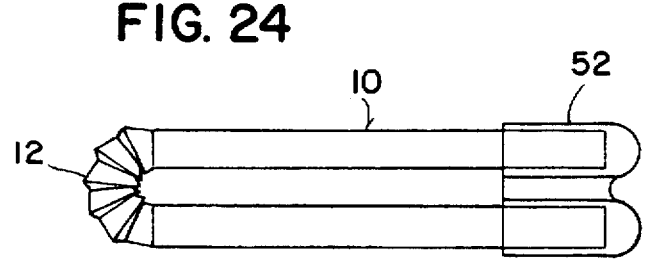
FIG. 24 shows a tenth embodiment, in which the opposite ends of the tubular inhaler is closed by a common closure cap.

In the embodiment shown in FIG. 24 the tubular inhaler 10 is stored in a condition in which the inhaler 10 is bent to a position in which the free ends of the inhaler are positioned closely adjacent, and the inhaler with the active substance therein is maintained in this position by means of a single closure member 52 which is closing both of the free ends of the inhaler. The closure member may, for example, be in the form of a pair of closure caps which are interconnected by a connecting portion which may be formed integrally with the closure caps. This embodiment secures that both of the opposite ends of the tubular inhaler 10 are opened before the inhaler can be used.

Figure 25:
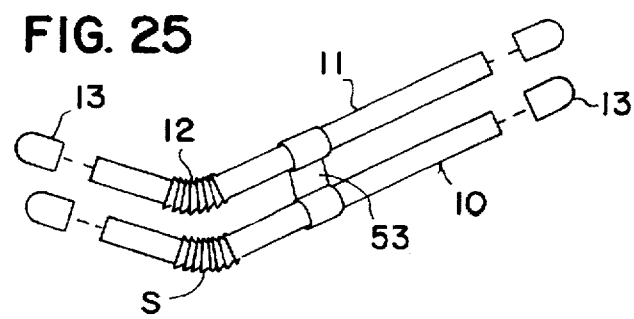
FIG. 25 shows a pair of spaced, interconnected inhalers to be inserted in the nostrils of a user.

FIG. 25 shows a pair of spaced inhalers 10 of the type shown in FIG. 1 interconnected by an interconnecting member 53, so that the inhalers are suited to be inserted in the nostrils of a user.

It should be understood that various amendments and modifications of the embodiments described above and shown in the drawings could be made without departing from the scope of the present invention. Thus, features described in connection with any of the embodiments shown could also be used in connection with one or more of the other embodiments shown. As an example, any of the embodiments may contain a sieve or grid 38 as shown in FIGS. 12 and 13 or other kinds of means for retaining larger particles. Furthermore, any of the tubular bodies shown may comprise separate passages for "false" or enveloping air. Similarly, any of the embodiments of the tubular body may be provided with a compressible bulb 15 as shown in FIG. 1d or any other kind of means for providing compressed air.

We claim:

1. An inhaler comprising:
a one piece tubular body, which has a mouthpiece section and is intended to be used only once, and which defines an air flow passage therein, the tubular body having substantially rectilinear sections, at least one intermediate bendable section comprising peripherally extending corrugations; and
a single dose only of an active, inhalable, particulate substance being arranged within the air flow passage, said dose being sealed or closed in relation to an ambient atmosphere by closure means which are to be removed or opened by a user prior to use, and a cross-sectional area of the flow passage defined in the tubular body being unobstructed and not exceeding 75 mm$^2$.

2. An inhaler according to claim 1, wherein the tubular body comprises a pair of corrugated bendable sections, which are spaced by a non-corrugated rectilinear tubular section, so that the tubular body may be bent into a substantial S-shape.

3. An inhaler according to claim 1, wherein the corrugations of the corrugated bendable section are of the type which in an axial sectional view defines relatively sharp valleys and peaks.

4. An inhaler according to claim 3, wherein the corrugations are substantially saw tooth shaped in an axial sectional view.

5. An inhaler according to claim 1, wherein the cross-sectional area of the flow passage does not exceed 70 mm$^2$.

6. An inhaler according to claim 5, wherein the cross-sectional area of the flow passage does not exceed 50 mm$^2$.

7. An inhaler according to claim 6, wherein the cross-sectional area of the flow passage is 7–35 mm$^2$.

8. An inhaler according to claim 1, wherein the flow passage has a substantially circular cross-section, the inner diameter of the flow passage being substantially the same along the length of the tubular body.

9. An inhaler according to claim 8, wherein the inhaler is formed similar to a drinking straw.

10. An inhaler according to claim 1, wherein the bottoms of the corrugations are provided with codes for assisting in obtaining a bend suitable for the individual user.

11. An inhaler according to claim 1, wherein the mouthpiece section has a length so as to extend during use from the teeth of the user to a position adjacent to the root of the user's tongue.

12. An inhaler according to claim 1, further comprising a bite piece formed on the outer surface of the tubular body for engaging with the upper jaw teeth of the user so as to position the inhaler in the oral cavity of the user.

13. An inhaler according to claim 12, wherein the bite piece is removably mounted on the tubular body.

14. An inhaler according to claim 12, wherein the shape of the bite piece is adapted to the teeth of the individual user.

15. An inhaler according to claim 1, wherein the tubular body is moveable from a retracted storage condition to an extended condition of use.

16. An inhaler according to claim 15, wherein the tubular body is provided with peripheral corrugations along a major part of its length so as to allow longitudinal stretching of the tubular body.

17. An inhaler according to claim 1, wherein the closure means comprise a pair of cap members removably mounted at opposite ends of the tubular body.

18. An inhaler according to claim 1, wherein the free ends of the tubular body are positioned closely adjacent, said free ends being closed by a common removable closure member.

19. An inhaler according to claim 17, wherein at least one of the cap members is made from a transparent material.

20. An inhaler according to claim 1, wherein the tubular body is at least partly made from a transparent material.

21. An inhaler according to claim 1, wherein the mouthpiece section of the tubular body is adapted to be inserted into a nostril of a user.

22. An inhaler according to claim 21 comprising a pair of tubular bodies and a connecting part for interconnecting the same, said one end or mouthpiece end of said pair of tubular bodies being arranged in spaced relationship so that said ends may be inserted into the nostrils of a user.

23. An inhaler comprising:
- a one piece tubular body, which has a mouthpiece section and is intended to be used only once, and which defines an air flow passage therein, the tubular body having a pair of substantially rectilinear sections and an intermediate curved section defining an obtuse angle between the rectilinear sections; and
- a single dose only of an active, inhalable, particulate substance being arranged within the air flow passage, said dose being sealed or closed in relation to a ambient atmosphere by closure means which are to be removed or opened by a user prior to use and a cross-sectional area of the flow passage defined in the tubular body being unobstructed and not exceeding 75 mm$^2$.

24. An inhaler according to claim 23, wherein the curved section of the tubular body comprises peripherally extending corrugations.

25. An inhaler according to claim 24, wherein the corrugations of the corrugated curved section are of the type which in an axial sectional view defines relatively sharp valleys and peaks.

26. An inhaler according to claim 25, wherein the corrugations are substantially saw tooth shaped in an axial sectional view.

27. An inhaler according to claim 23, wherein the cross-sectional area of the flow passage does not exceed 70 mm$^2$.

28. An inhaler according to claim 27, wherein the cross-sectional area of the flow passage does not exceed 50 mm$^2$.

29. An inhaler according to claim 28, wherein the cross-sectional area of the flow passage is 7–35 mm$^2$.

30. An inhaler according to claim 29, wherein the cross-sectional area of the flow passage is about 20 mm$^2$.

31. An inhaler according to claim 7, wherein the cross-sectional areas of the flow passage is about 20 mm$^2$.

32. An inhaler according to claim 23, wherein the flow passage has a substantially circular cross-section, the inner diameter of the flow passage being substantially the same along the length of the tubular body.

33. An inhaler according to claim 29, wherein the inhaler is formed similar to a drinking straw.

34. An inhaler according to claim 23, further comprising means for imparting to air flowing through the flow passage a rotational movement about the longitudinal axis of the flow passage.

35. An inhaler according to claim 23, wherein the mouthpiece section has a length so as to extend during use from the teeth of the user to a position adjacent to the root of the user's tongue.

36. An inhaler according to claim 23, further comprising a bite piece formed on the outer surface of the tubular body for engaging with the upper jaw teeth of the user so as to position the inhaler in the oral cavity of the user.

37. An inhaler according to claim 36, wherein the bite piece is removably mounted on the tubular body.

38. An inhaler according to claim 37, wherein the shape of the bite piece is adapted to the teeth of the individual user.

39. An inhaler according to claim 23, wherein the closure means comprise a pair of cap members removably mounted at opposite ends of the tubular body.

40. An inhaler according to claim 39, wherein the free ends of the tubular body are positioned closely adjacent, said free ends being closed by a common removable closure member.

41. An inhaler according to claim 39, wherein at least one of the cap members is made from a transparent material.

42. An inhaler according to claim 23, wherein the tubular body is at least partly made from a transparent material.

43. An inhaler according to claim 23, wherein the mouthpiece section of the tubular body is adapted to be inserted into a nostril of a user.

44. An inhaler according to claim 43 comprising a pair of tubular bodies and a connecting part for interconnecting the same, said one end or mouthpiece end of said pair of tubular bodies being arranged in spaced relationship so that said ends may be inserted into the nostrils of a user.

* * * * *

(12) REEXAMINATION CERTIFICATE (4252nd)
United States Patent
Keldmann et al.

(10) Number: US 5,797,392 C1
(45) Certificate Issued: Jan. 9, 2001

(54) INHALER

(75) Inventors: Erik Keldmann, Odense; John Reipur, Klampenborg, both of (DK)

(73) Assignee: Direct-Haler A/S, Odense (DK)

Reexamination Request:
No. 90/005,427, Jul. 21, 1999

Reexamination Certificate for:
Patent No.: 5,797,392
Issued: Aug. 25, 1998
Appl. No.: 05/785,960
Filed: Jan. 22, 1997

Related U.S. Application Data

(63) Continuation-in-part of application No. PCT/DK96/00034, filed on Jan. 22, 1996.

(51) Int. Cl.$^7$ .................................................. A61M 15/00
(52) U.S. Cl. .......................... 128/203.15; 128/203.23; 128/203.12
(58) Field of Search .................. 128/200.12, 202.21, 128/203.15, 203.21, 203.22, 203.23, 207.14, 912; 239/33, 587.1, 588; 222/464.3; 131/176, 214, 222, 348, 191, 192

(56) References Cited

U.S. PATENT DOCUMENTS

| | | | |
|---|---|---|---|
| 419,942 | * | 1/1890 | Harding . |
| 487,873 | | 12/1892 | Blackman . |
| 862,732 | | 8/1907 | Hall . |
| 1,062,786 | * | 5/1913 | Miller . |
| 1,540,274 | | 6/1925 | Moore . |
| 2,021,332 | | 11/1935 | Silten . |
| 2,086,588 | * | 7/1937 | Tobin et al. . |
| 2,503,732 | | 4/1950 | Heisllerkamp . |
| 2,589,504 | | 3/1952 | Miller . |
| 2,669,988 | | 2/1954 | Carpenter . |
| 2,693,182 | | 11/1954 | Phillips . |
| 2,756,742 | | 7/1956 | Barton . |
| 2,820,457 | | 1/1958 | Phillips . |
| 2,857,911 | | 10/1958 | Bennett . |
| 2,908,269 | | 10/1959 | Cheng . |
| 3,013,554 | | 12/1961 | Safar et al. . |
| 3,139,088 | | 6/1964 | Galleher . |
| 3,154,069 | | 10/1964 | Ring . |
| 3,326,695 | * | 6/1967 | Neuhauser ................ 239/33 |
| 3,409,224 | * | 11/1968 | Harp et al. ................ 239/33 |
| 3,602,227 | | 8/1971 | Andrew . |
| 3,742,939 | | 7/1973 | Sayer . |
| 3,749,312 | * | 7/1973 | Panzer ................ 239/33 |

(List continued on next page.)

FOREIGN PATENT DOCUMENTS

| | | | | |
|---|---|---|---|---|
| 311922 | * | 6/1926 | (DE) | ............... 128/203.22 |
| 669840 | | 12/1938 | (DE) . | |
| 741542 | | 9/1943 | (DE) . | |
| 27 16 323 | | 10/1978 | (DE) . | |
| 2815039 | | 12/1978 | (DE) . | |
| 0 404 454 | | 12/1990 | (EP) . | |
| 0 695 561 A1 | | 2/1996 | (EP) . | |
| 606004 | * | 6/1926 | (FR) | ............... 604/58 |
| 2 270 293 | | 3/1994 | (GB) . | |
| 177146 | | 8/1982 | (HU) . | |
| 215 800 | | 3/1999 | (HU) . | |
| WO 89/01348 | | 2/1989 | (WO) . | |
| WO 92/20391 | | 11/1992 | (WO) . | |
| WO 93/17728 | | 9/1993 | (WO) . | |
| WO 94/05358 | | 3/1994 | (WO) . | |
| WO 96/22802 | | 8/1996 | (WO) . | |

OTHER PUBLICATIONS

International Search Report mailed Oct. 2, 1998.

*Primary Examiner*—Aaron J. Lewis

(57) ABSTRACT

An inhaler comprises a tubular body in which an air flow passage is defined. A single dose of an active, inhalable, particulate substance is arranged within the air flow passage and is sealed or closed in relation to the ambient atmosphere by closure means, such as removable caps, a section of the flow passage extending from a free mouthpiece end of the tubular body along a major part of the total length of the flow passage is preferable 7–35 mm$^2$, for example about 20 mm$^2$. The inhaler may be adapted to be used only once, and the tubular body of the inhaler may be a length of a simple tube similar to a drinking straw.

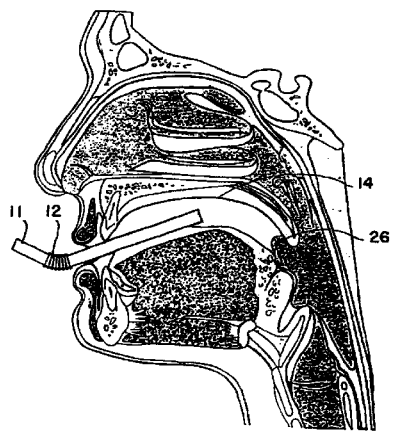

U.S. PATENT DOCUMENTS

| | | |
|---|---|---|
| 3,756,244 | 9/1973 | Kinnear et al. . |
| 3,760,811 | 9/1973 | Andrew . |
| 3,993,081 | 11/1976 | Cussell . |
| 4,068,658 | 1/1978 | Berman . |
| 4,142,527 | 3/1979 | Garcia . |
| 4,148,308 | 4/1979 | Sayer . |
| 4,167,946 | 9/1979 | Sandstrom . |
| 4,216,768 | 8/1980 | Jack ................. 128/203.15 |
| 4,265,236 | 5/1981 | Pacella ............... 128/203.23 |
| 4,270,529 | 6/1981 | Muto . |
| 4,286,607 * | 9/1981 | Claessens ............... 131/328 |
| 4,356,927 * | 11/1982 | Cooper et al. ............ 239/33 |
| 4,593,690 * | 6/1986 | Sheridan et al. ......... 128/912 |
| 4,944,317 * | 7/1990 | Thal ...................... 131/348 |
| 5,334,348 * | 8/1994 | Saito et al. ............... 239/33 |
| 5,718,681 * | 2/1998 | Manning ................. 239/33 |

\* cited by examiner

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–44 is confirmed.

* * * * *